5-(4-BROMOPHENYL)OXAZOLE

This invention is concerned with the chemical compound 5-(4-bromophenyl)oxazole.

This compound possesses antifungal activity and is useful in the prevention and eradication of fungal growth. It is particularly inimical to the growth of *Aspergillus niger* in the commonly employed in vitro technique for determining antifungal properties at a level of 100 mcg of compound per milliliter of test media.

The compound of this invention is readily formulated in known fashion with various compatible excipients and adjuvants to provide antifungal compositions.

In order that this invention may be readily available to and understood by those skilled in the art, the following example illustrates the now preferred method of making it.

A. Ethyl [[2-(4-Bromophenyl)-2-oxoethyl]amino]oxoacetate (1) To α,p-dibromoacetophenone (200 g, 0.72 mole) and chloroform (1500 ml) was added hexamethylenetetramine (100 g, 0.72 mole) and the mixture was stirred at room temperature for 4.0 hours. Solid was collected by filtration and air-drying gave 295 g of crude addition product.

A mixture of the above addition product (295 g), methanol (600 ml) and conc. HCl (820 ml) was stirred for 24 hours and collected. Recrystallization from 2N HCl and drying at 60° gave 131 g (0.52 mole) of α-amino-p-bromoacetophenone hydrochloride (72%), m.p. 278°–283°.

(2) α-Amino-p-bromoacetophenone hydrochloride (50 g, 0.2 mole), ethyl oxalyl chloride (25 ml, 0.22 mole) and dry benzene (200 ml) were maintained at reflux for 4.0 hours and the hot mixture was filtered. After cooling, solid was collected, and recrystallization from benzene gave 43.9 g (0.14 mole) (70% yield in two crops, overall yield 50%), m.p. 131°–133°.

Anal. Calcd. for $C_{12}H_{12}BrNO_4$: C, 45.88; H, 3.85; N, 4.46. Found: C, 45.86; H, 3.73; N, 4.55.

B. Ethyl 5-(4-Bromophenyl)-2-oxazolecarboxylate

A mixture of ethyl [[2-(4-bromophenyl)-2-oxoethyl]amino]oxoacetate (35 g, 0.11 mole) and phosphorus oxychloride (150 ml) was maintained at reflux for 10.5 hours and cooled to room temperature. The solution was poured into a mixture of ice and water (3 liter) and stirred for 1.0 hour. The resulting solid was collected by filtration and air-dried. Recrystallization from methylcyclohexane gave 22.3 g (0.075 mole) of product (yield, 68%), m.p. 119.5°–122°.

Anal. Calcd. for $C_{12}H_{10}BrNO_3$: C, 48.67; H, 3.40; N, 4.73. Found: C, 48.79; H, 3.46; N, 4.78.

C. 5-(4-Bromophenyl)oxazole

A stirred mixture of ethyl 5-(4-bromophenyl)-2-oxazolecarboxylate (150 g. 0.51 mole), ethanol (500 ml) and 10% NaOH (250 ml) was maintained at reflux for 2.0 hours, then cooled. To the cold mixture ($\leq 5°$), conc. HCl was added dropwise until an acid pH was obtained, and stirring was continued for 2.0 hours. The solid was collected by filtration and air drying gave 115.0 g (0.43 mole) of crude intermediate.

A stirred solution of the intermediate sodium salt (20.0 g, 0.07 mole) and toluene (600 ml) was warmed to 40°–50°. Concentrated HCl (20 ml) was added and the mixture was maintained at reflux for 3.0 hours while water was removed with a Dean Stark trap. The cooled, filtered solution was concentrated by vacuum distillation to a solid residue. Recrystallization from methylcyclohexane gave 9.4 g (0.04 mole, 57%) of the product in two crops, m.p. 77°–80°.

Anal. Calcd. for $C_9H_6BrNO$: C, 48.24; H, 2.70; N, 6.25. Found: C, 48.20; H, 2.60; N, 6.15.

What is claimed is:

1. The compound 5-(4-Bromophenyl)oxazole.

* * * * *

United States Patent [19]

White, Jr,

[11] 4,171,307

[45] Oct. 16, 1979

[54] 5-(4-BROMOPHENYL)OXAZOLE

[75] Inventor: Ralph L. White, Jr,, Norwich, N.Y.

[73] Assignee: Morton-Norwich Products, Inc., Norwich, N.Y.

[21] Appl. No.: 960,076

[22] Filed: Nov. 13, 1978

[51] Int. Cl.$^2$ .................................... C07D 263/32
[52] U.S. Cl. ................... 548/235; 424/272; 548/236
[58] Field of Search .................... 260/307 R

[56] References Cited

U.S. PATENT DOCUMENTS 2,895,959 7/1959 Jeffreys et al. ................ 260/307

OTHER PUBLICATIONS

Tanaka, C.A. 62, 16222d (1965).

Primary Examiner—Raymond V. Rush
Attorney, Agent, or Firm—Anthony J. Franze

[57] ABSTRACT

The compound 5-(4-bromophenyl)oxazole is useful as an antifungal agent.

1 Claim, No Drawings